United States Patent [19]
Beck et al.

[11] Patent Number: 5,499,964
[45] Date of Patent: Mar. 19, 1996

[54] SPECULUM WITH SMOKE EVACUATION CHANNEL

[75] Inventors: Henry Beck, Skaneateles; J. Brian Noll, Marcellus; Michael D. Lynch, Skaneateles, all of N.Y.

[73] Assignee: Welch Al Iyn, Inc., Skaneateles Falls, N.Y.

[21] Appl. No.: 307,262

[22] Filed: Sep. 16, 1994

[51] Int. Cl.$^6$ ............................. A61B 1/06; A61B 1/303; A61B 1/32
[52] U.S. Cl. ........................... 600/220; 600/223; 600/205
[58] Field of Search ...................................... 600/199–224

[56] References Cited

U.S. PATENT DOCUMENTS

| | | | |
|---|---|---|---|
| 2,672,859 | 3/1954 | Jones . | |
| 3,716,047 | 2/1973 | Moore et al. | 600/222 |
| 3,889,661 | 6/1975 | Fiore | 128/6 |
| 4,884,559 | 12/1989 | Collins . | |
| 4,971,036 | 11/1990 | Collins . | |
| 5,026,368 | 6/1991 | Adair | 606/15 |
| 5,063,908 | 11/1991 | Collins . | |
| 5,143,054 | 9/1992 | Adair | 128/18 |
| 5,154,166 | 10/1992 | Chikama | 128/4 |
| 5,329,935 | 7/1994 | Takahashi | 128/4 |

*Primary Examiner*—Richard J. Apley
*Assistant Examiner*—Kelly M. McGlashen
*Attorney, Agent, or Firm*—Harris Beach & Wilcox

[57] ABSTRACT

An improved vaginal speculum includes a lower blade member having a straight segment, a curved portion, and a hollow leg portion. The speculum also includes a slide member, an upper blade member rotatably and slidably movable relative to lower blade member, and a light pipe extending from the hollow leg toward the straight segment of the lower blade. The light pipe is adapted to direct light from a light source positionable within the leg, into a region under examination. The upper blade is provided with a smoke evacuation passage formed by a U-shaped channel member positioned adjacent a contoured interior surface of the upper blade member. The U-shaped channel member is provided with a forward end, a rearward end, a bottom surface, and a pair of opposed side walls each having a top edge shaped to fit snugly against the contours of the interior surface or retaining walls formed thereon. The U-shaped channel member quickly snap fits into the upper blade which has a conventional configuration that is easily formed by injection molding.

7 Claims, 5 Drawing Sheets

SPECULUM WITH SMOKE EVACUATION CHANNEL

BACKGROUND OF THE INVENTION

1. Field of the Invention

This invention relates in general to specula and, in particular, to vaginal specula. More specifically, but without restriction to the particular embodiments hereinafter described in accordance with the best mode of practice, this invention relates to a vaginal speculum including a smoke evacuation channel for efficiently removing smoke from an area undergoing a smoke producing medical procedure.

2. Discussion of the Related Art

Various surgical techniques have recently developed with the advent of electrosurgical technologies. Among these surgical techniques are those involving gynecological procedures such as, for example, hysterectomies and surgical treatment of cervical cancers. During this type of gynecological procedure, a vaginal speculum is typically employed to dilate the vaginal cavity so that the uterus or cervix may be operated upon in an unobstructed manner. Electrosurgical tools are then employed to carry out the extent of surgery required.

Electrosurgical techniques involve vaporization of tissue which necessarily produces some amount of smoke. This smoke can obscure the surgeon's view of the area undergoing surgery. In the area of gynecological surgery, there has thus been previously proposed vaginal specula including smoke tubes for removing the smoke produced by electrosurgical procedures. Such devices include the surgical speculum disclosed in U.S. Pat. No. 4,884,559 which issued Dec. 5, 1989 to J. H. Collins. The Collins speculum includes a lower blade and an upper blade which is provided with a separately mounted smoke tube or an internally formed hollow, each of which extends over substantially the entire length of the upper blade.

Prior vaginal specula incorporating smoke evacuation systems have employed smoke tubes that are either welded or soldered to metal specula, solvent bonded to plastic specula blades, or in the case of the Collins device, require additional fasteners spaced along the upper blade. These tube systems have limited rates of evacuation due to relatively small tube diameters and require a fastening means which involves added assembly time or manufacturing expense. Collins proposes an alternate smoke evacuation system for a speculum which includes a hollow formed in the upper blade. While this system provides added volume capacity for increasing the rate of smoke evacuation, this type of doubled walled upper blade with the hollow formed therebetween requires complicated and expensive machining or injection molding processes.

OBJECTS AND SUMMARY OF THE INVENTION

It is, therefore, an object of the present invention to improve vaginal specula.

Another object of this invention is to prevent smoke produced by electrosurgical procedures from obscuring the surgeon's view of an area undergoing surgery.

It is a further object of the present invention to reduce the assembly time of providing a vaginal speculum with a smoke evacuation system.

Still another object of the present invention is to simplify the structure of a smoke evacuation system employed in a vaginal speculum for use during a smoke producing medical procedure.

It is yet a further object of the present invention to rapidly evacuate smoke from a site undergoing electrosurgical procedures so that the surgeon's view of the site is not obscured during the procedure.

Yet another object of the present invention is to efficiently evacuate smoke through a vaginal speculum including an illumination system for illuminating an area undergoing surgery.

An additional object of the present invention is to evacuate smoke through a vaginal speculum including an illumination system for illuminating an area undergoing surgery so that light illuminating the area under surgery is not obscured by the smoke.

These and other objects are attained in accordance with the present invention wherein there is provided an improved vaginal speculum for use during diagnostic and surgical procedures. The present speculum includes a lower blade member having a straight segment, a curved portion, and a hollow leg portion. The speculum also includes a slide member, an upper blade member rotatably and slidably movable relative to lower blade member, and a light pipe extending from the hollow leg toward the straight segment of the lower blade. The light pipe is adapted to direct light from a light source positionable within the leg, into a region under examination. According to one aspect this invention, the present speculum is provided with a smoke evacuation passage formed by a U-shaped channel member positioned adjacent a contoured interior surface of the upper blade member. The U-shaped channel member is provided with a forward end, a rearward end, a bottom surface, and a pair of opposed side walls each having a top edge shaped to fit snugly against the contours of the interior surface. The U-shaped channel member quickly snap fits into the upper blade which has a conventional configuration that is easily formed by injection molding.

In accordance with further aspects of a preferred embodiment of the present invention, the vaginal speculum is also provided with a adjustable extension system that includes a pawl projecting from the slide member and a series of ratchet teeth formed on the leg portion. These teeth are engagable with the slide member pawl which is biased toward the leg portion teeth. The adjustable extension system locks the slide member in an adjusted position relative to the leg portion to position the upper blade in an extended position relative to the lower blade. An adjustable rotation system is also provided. This system includes a lever portion projecting from the upper blade adjacent its pivotal connection with the slide member and a curved ratchet-toothed tongue projecting from the slide member toward the lever portion. The lever portion is provided with a pawl engagable by the ratchet teeth of the tongue which is biased toward the lever portion pawl by the resiliency of the plastic material forming the slide member. The adjustable rotation system locks the blade members in an adjusted angular position relative to each other to provided a desired degree of dilation.

One preferred embodiment of the upper blade of the present vaginal speculum is provided with a pair of retaining walls. These retaining walls contain the opposed side walls of the U-shaped channel member in a snug sliding fit when the channel member is snapped into the upper blade. In this manner, a leak-tight smoke passage is formed between the forward and rearward ends of the U-shaped channel member.

BRIEF DESCRIPTION OF THE DRAWING

Further objects of the present invention together with additional features contributing thereto and advantages accruing therefrom will be apparent from the following description of the preferred embodiments of the invention which is shown in the accompanying drawing, wherein.

DETAILED DESCRIPTION OF THE PREFERRED EMBODIMENTS

Figure 1:
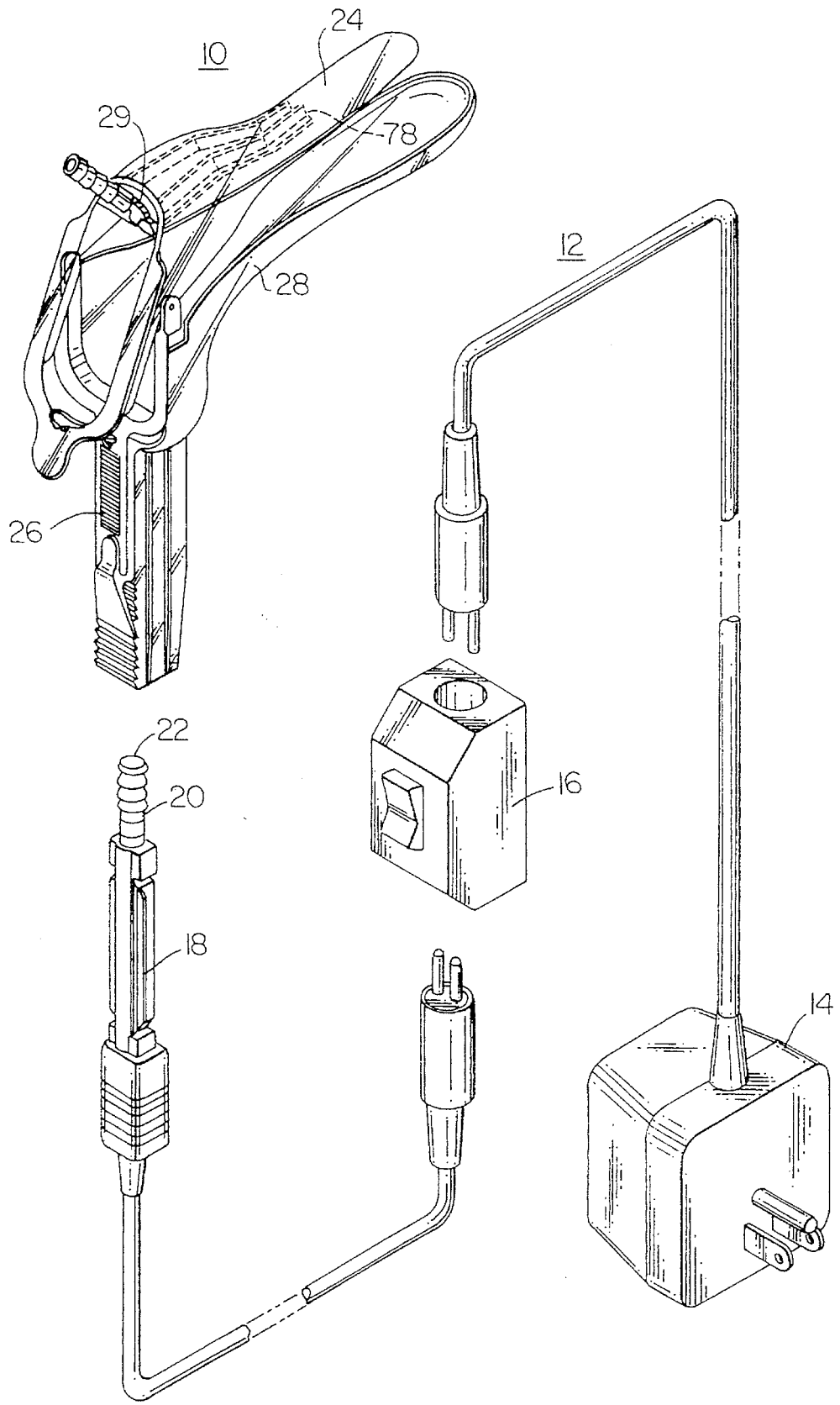
FIG. 1 is a perspective view of a vaginal speculum according to the present invention, and an illumination system employed in conjunction therewith.

Referring now to the drawing and initially to FIG. 1, there is shown a vaginal speculum 10 in accordance with the present invention. The speculum 10 is illustrated in conjunction with a illumination system generally referenced 12. The speculum 10 and the illumination system 12 are both commercially available through Welch Allyn, Inc. of Skaneateles Falls, N.Y. For conveniently and clearly describing the present invention, the various directional references used herein are taken relative to the reference frame of the drawing, it being understood that in actual use of the present device, relative directional references may be rotated into different spacial orientations or otherwise redirected.

The illumination system 12 includes an AC wall transformer 14, an on/off switch 16, and a lamp assembly 18. The lamp assembly 18 includes a distal end segment 20 which is provided with a lamp 22. The lamp 22 is preferably a miniature or sub-miniature low wattage metal halide lamp. The speculum 10, as shown in FIG. 1, is comprised of three main component parts which include an upper blade 24, a slide member 26, and a lower blade 28. In accordance with the present invention, the upper blade 24 is provided with a smoke evacuation assembly 29 which will be described below in further detail. The upper blade 24 and the lower blade 28 are preferably formed from a relatively ridged transparent plastic material while the slide member 28 is preferably formed from a relatively flexible plastic material.

Figure 2:
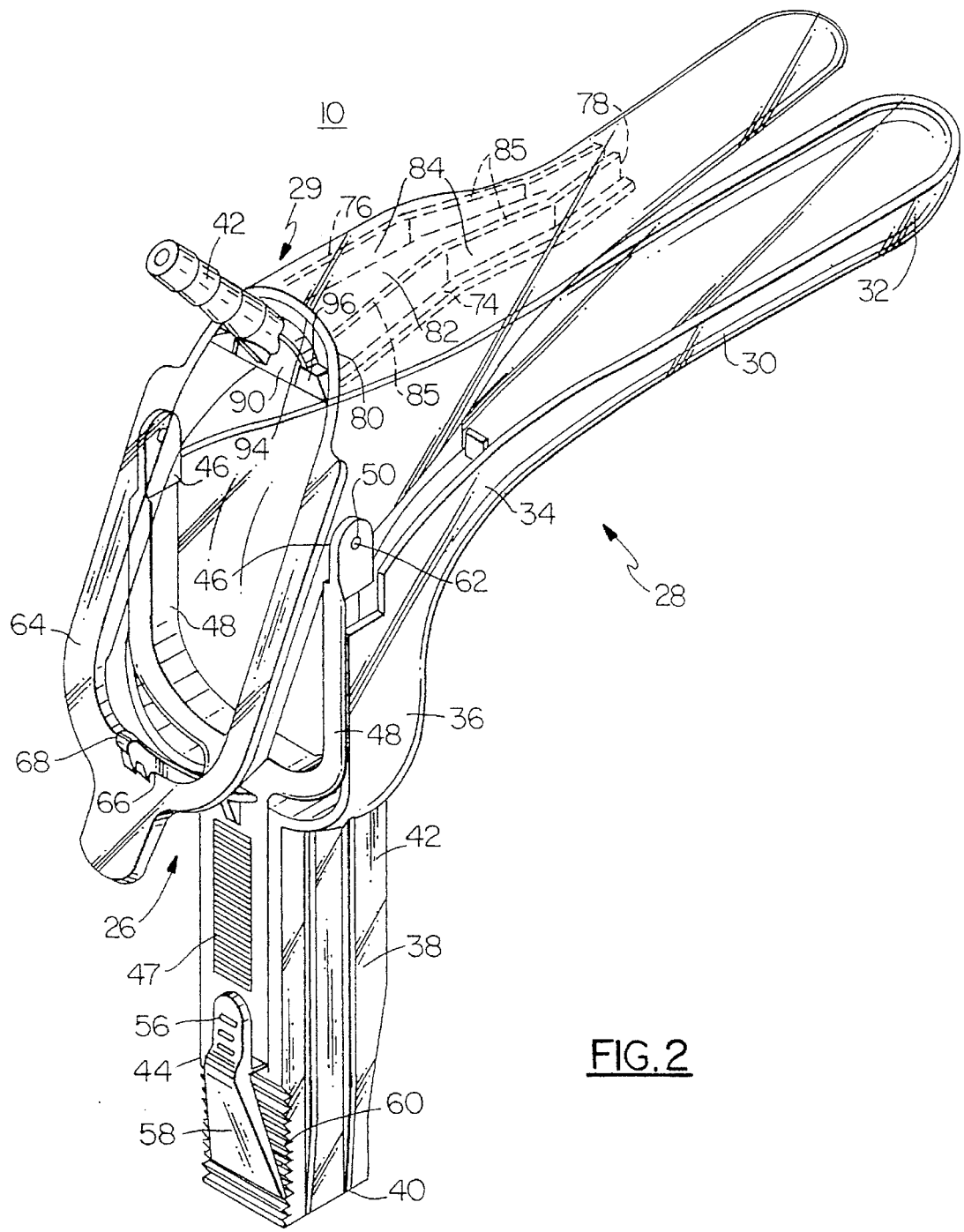
FIG. 2 is a detailed isolated perspective view of the vaginal speculum illustrated in FIG. 1.

FIG. 2 shows that the lower blade 28 includes a straight segment 30 having a distal tip 32 and a proximal end 34. The distal tip 32 and proximal end 34 of the straight segment 30 define a longitudinal axis extending through these two locations. The lower blade 28 also includes a curved channel segment 36 extending downwardly from the proximal end 34 of the straight segment 30. The curved channel segment 36 extends into a depending hollow leg portion 38 which has a distal end 40 and a proximal end 42 integrally formed into a lower end of the curved channel segment 36. The distal end 40 of leg 38 is open and adapted to receive therein, the lamp assembly 18 to position the lamp 22 adjacent the proximal end 42 of the leg 38.

Figure 4:
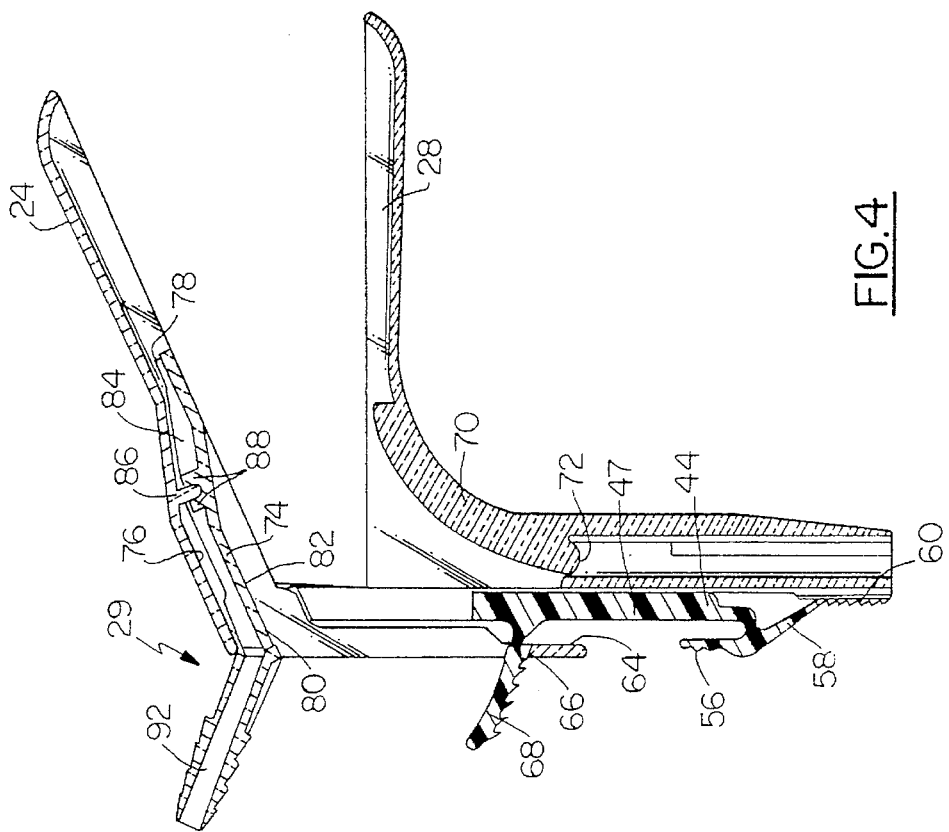
FIG. 4 is a cross sectional side elevation view of the vaginal speculum illustrated in FIG. 3, this view showing a light pipe for use in conjunction with the illumination system of FIG. 1.
Figure 3:
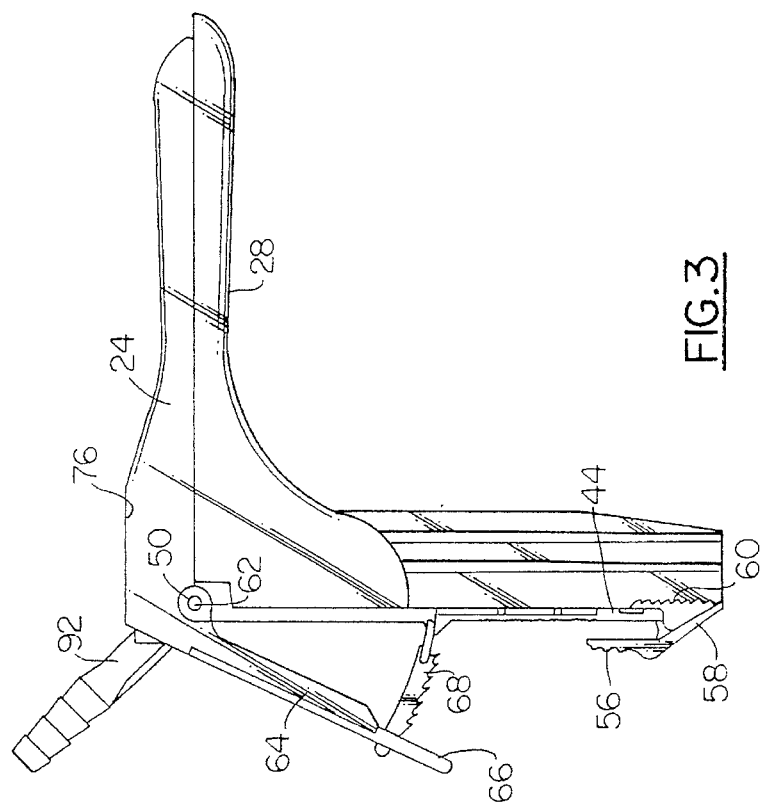
FIG. 3 is a side elevation view of the vaginal speculum according to the present invention.
Figure 7:
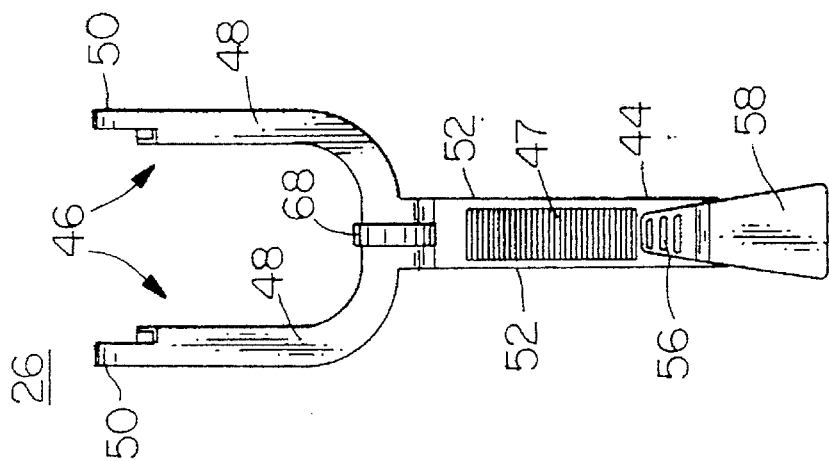
FIG. 7 is a front elevation of the slide member illustrated in FIG. 6.
Figure 6:
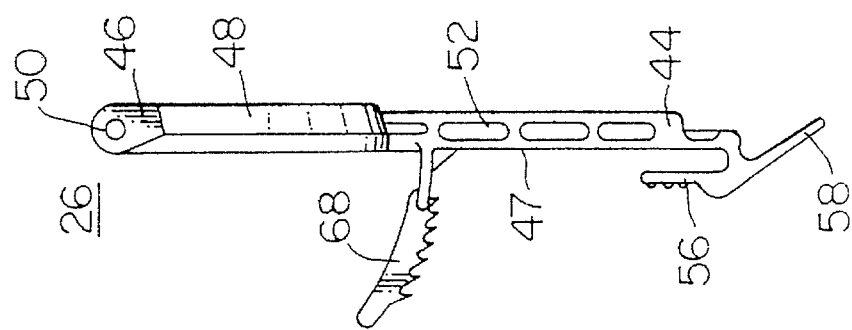
FIG. 6 is a side elevation view of a slide member forming part of the present vaginal speculum.
Figure 5:
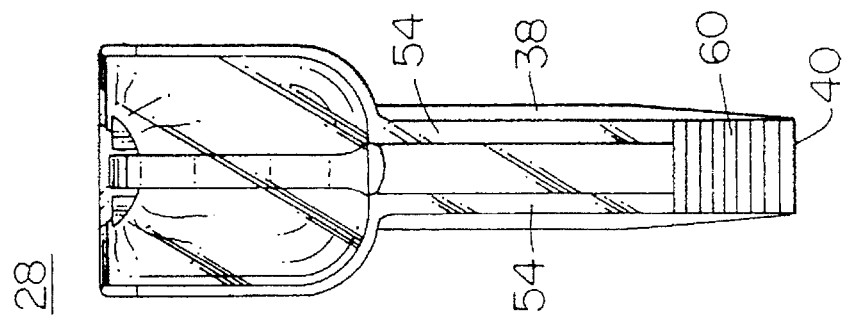
FIG. 5 is a rear elevation view of the lower blade of a vaginal speculum in accordance with the present invention.

With continuing reference to FIG. 2 as viewed now in conjunction with FIGS. 3 through 7, it is shown that the slide member 26 includes a distal end 44 and a forked proximal end 46. The forked proximal end 46 is secured to a lower center segment 47 and is comprised of a pair of arms 48—48. FIGS. 2, 3 and 6 show that each of the arms 48 includes an opening 50. As best shown in FIGS. 6 and 7, the lower center segment 47 of the slide member 26 is provided with a pair edge slots 52—52, while the hollow leg portion 38 of the lower blade 28 includes a pair of vertical lip segments 54—54 (FIG. 5). The slide member 26 is assembled with the lower blade 28 by inserting the pair edge slots 52—52 of the lower center segment 47 between the pair of vertical lip segments 54—54. The distal end 44 of the slide member 26 is provided with a lever 56 that includes a pawl 58. The distal end 40 of the hollow leg portion 38 is provided with a series of ratchet teeth 60 as shown in FIGS. 2 to 5. As a result of the relatively flexible material forming the slide member 26, the lever 56 may be squeezed toward the lower central segment 47 to move the pawl 58 outwardly from its rest position shown in FIGS. 6 and 7. In this manner, the slide member 26 is movable up and down the hollow leg portion 38 from a lower position shown in FIG. 3 to an extended position shown in FIG. 4.

Figures 8, 9:
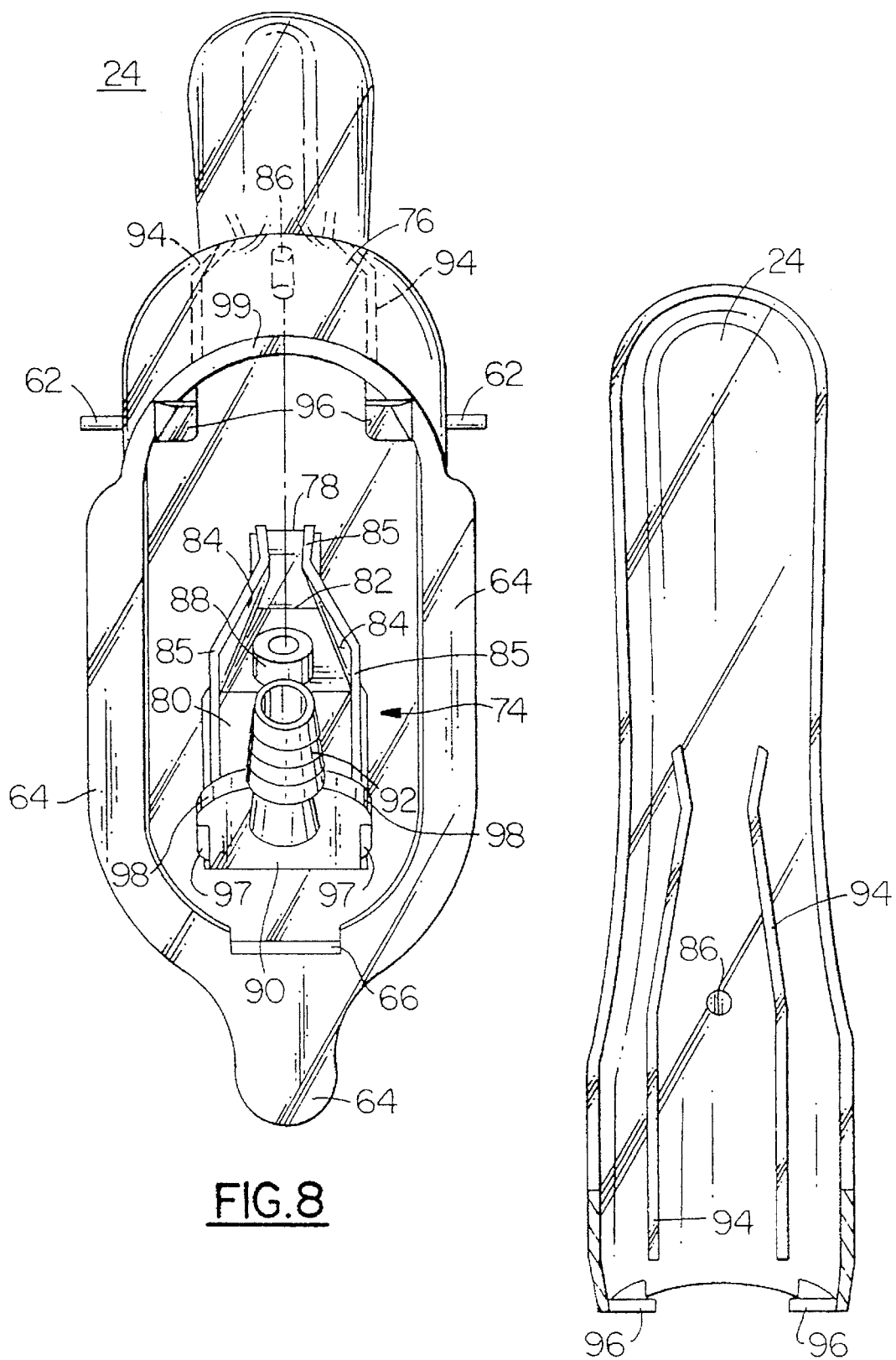
FIG. 8 is a perspective view of the upper blade of the vaginal speculum according to the present invention, this view taken from the rear of the upper blade and showing the smoke evacuation assembly exploded away from the blade.
FIG. 9 is a partially broken away plan view of the interior side of one embodiment of the upper blade of the vaginal speculum according to this invention.

As best shown in FIGS. 2, 3, and 8, the upper blade 24 is provided with a pair of extending pin segments 62. The upper blade 24 also includes a lever portion 64 with a central pawl 66 as shown in FIGS. 2, 3, 4, and 8. The upper blade 24 is rotatably secured to the slide member 26 by assembling these two elements together with the extension pins 62 inserted into the openings 50 on the arms 48 of the forked proximal end 46 of the slide member 26. The upper blade 24 is rotatably adjustable relative to the lower blade 28 by use of a curved ratchet-toothed tongue 68 that extends outwardly from the top of the lower center segment 47 of the slide member 26. The upper blade 24 is rotatably adjusted relative to the lower blade 28 by moving the lever portion 64 toward the hollow leg portion of the lower blade 28. This action causes the pawl 66 of the lever portion 64 to move passed consecutive teeth on the curved ratchet-toothed tongue 68. Thus the upper blade 24 is both extendable and rotatable relative to the lower blade 28. The fully extended and rotated position of the speculum 10 is shown in FIG. 4.

FIGS. 2 through 6 illustrate that the teeth of the series of ratchet teeth 60 are biased upwardly toward the slide member pawl 58. In a similar manner, the teeth formed on the curved ratchet-toothed tongue 68 are biased toward the lower center segment 47 of the slide member 26. Movement of the lever portion 64 is thus biased toward the hollow leg portion 38 while movement of the slide member 26 is biased upwardly. The biased position of the upper blade 24 relative to the lower blade 28 may be released by depressing the lever 56 or slightly deflecting upwardly the end of the curved ratchet-toothed tongue 68. During use of the speculum 10, the vaginal cavity will press against the blades 24 and 28 to provide a sufficient resistance force which will hold the pawls 58 and 66 securely against a respective tooth. The slide member 26, its pawl 58, and its curved ratchet-toothed tongue 68 are formed as a single-piece unit from the preferably relatively flexible plastic material referenced above.

As shown in FIG. 4, the lower blade 28 includes a light pipe 70 having a light-receiving optical surface 72 which is generally hemispherical in shape. The light pipe 70 is formed within the curved channel segment 36 and extends from the proximal end 42 of the hollow leg portion 38 to a location adjacent the proximal end 34 of the straight segment 30. During use of the speculum 10, the lamp assembly 18 is positioned within the hollow leg portion 38 and the lamp 22 activated by means of switch 16. Light emanating from the lamp 22 is directed into the light-receiving optical surface 72 of the light pipe 70 and directed into the straight segment 30 of the lower blade 28. In this manner, medical personnel using the device are provided with illumination for illuminating the interior of the vaginal cavity undergoing diagnosis or surgery.

The smoke evacuation assembly 29, will now be discussed in detail with particular reference to FIGS. 2, 4, 8, and 9. The smoke evacuation assembly 29 includes a U-shaped channel member 74 which is positioned adjacent a contoured interior surface 76 of the upper blade 24. The U-shaped channel member 74 is provided with a forward end 78, a rearward end 80, a bottom surface 82, and a pair of opposed side walls 84—84 each having a top edge 85 shaped, in one preferred embodiment, to fit snugly against the contoured interior surface 76 of the upper blade 24. The upper blade 24 is provided with a center pin 86 while the bottom surface 82 of the U-shaped channel member 74 is provided with an annular boss 88 shown in FIGS. 4 and 8. The rearward end 80 of the U-shaped channel member 74 is provided with a end wall 90 as best shown in FIGS. 2 and 8. The end wall 90 is provided with a tubular nipple 92 adapted to connect to a suction hose.

In an alternate preferred embodiment, the upper blade 24 is further provided with a pair of interlocking or retaining walls 94—94 as best shown in FIG. 9. Each embodiment of the upper blade 24 includes a pair of snap tabs 96—96 as shown in FIGS. 8 and 9. The end wall 90 of the U-shaped channel member 74 is also provided with a pair of corresponding edge notches 97—97, FIG. 8.

The smoke evacuation assembly is assembled to the upper blade 24 by a snap fit provided between the center pin 86 and the annular boss 88, and between the snap tabs 96 and each corresponding edge notch 97. In this assembled condition, the top edges 85 of the pair of opposed side walls 84—84 fit snugly against or adjacent the contoured surface 76 of the upper blade 24 while the opposed side walls 84 are snugly interlocked by the retaining walls 94 of the upper blade shown in FIGS. 8 and 9. A top edge 98 of the end wall 90 fits snugly against an arched segment 99 formed by the lever portion 64 and the upper blade 24. The end wall 90 is retained against the arched segment 99 by virtue of the snap tabs 96 snapping into and seating within the edge notches 97. In this manner, the U-shaped channel member 74 forms a leak-tight smoke evacuation passage from the forward end 78 out through the tubular nipple 92. Suction provided to the tubular nipple 92 will induce the flow of smoke through the smoke evacuation passage so that smoke is removed therethrough while being substantially retained by the U-shaped channel member 74. The size of the U-shaped channel member 74 is selected to provide a sufficient rate of smoke removal so that smoke produced during a surgical procedure will not obscure proper functioning of the light pipe 70 and the light receiving optical surface 72 when illuminated by the lamp assembly 18.

While this invention has been described in detail with reference to certain preferred embodiments, it should be appreciated that the present invention is not limited to those precise embodiments. Rather, in view of the present disclosure which describes the best mode for practicing the invention, many modifications and variations would present themselves to those of skill in the art without departing from the scope and spirit of this invention, as defined in the following claims.

What is claimed is:

1. An improved vaginal speculum for use during surgery, said speculum comprising:

a lower blade member having a longitudinal axis extending through a distal tip end and being formed of a relatively rigid, transparent plastic material, said lower blade member further including a depending hollow leg portion having a distal end and a proximal end;

a slide member formed of a relatively flexible plastic material, said slide member having a distal end and a forked proximal end, said lower blade member and said slide member having cooperating engagement means for slidably connecting said slide member to the leg portion of the lower blade;

an upper blade member being formed of a relatively rigid, transparent plastic material and pivotally carried by said forked proximal end of said slide member, said upper blade member thereby being rotatably and slidably movable relative to said lower blade member;

a smoke evacuation passage formed by a U-shaped channel member positioned adjacent a contoured interior surface of said upper blade member, said U-shaped channel member including a forward end, a rearward end, a bottom surface, and a pair of opposed side walls each having a top edge shaped to fit snugly adjacent the contours of the interior surface so that smoke being removed through the evacuation passage travels from said forward end toward said rearward end while being substantially retained within said U-shaped channel member and a pair of retaining walls formed along said contoured interior surface of said upper blade member, said retaining walls providing an interlocking sliding fit with said pair of opposed side walls of said U-shaped channel member.

2. The speculum according to claim 1 further including a light pipe extending from the proximal end of the hollow leg portion toward the distal end tip of said lower blade member and terminating in a light-emitting optical surface disposed substantially perpendicular to the longitudinal axis of said lower blade member, said light pipe having a light-receiving optical surface adjacent the proximal end of the hollow leg portion adapted to receive light from a light source disposed within the leg portion whereby light from said light-emitting optical surface is substantially free from optical interference during smoke removal through said smoke evacuation passage.

3. The speculum according to claim 1 wherein the rearward end of said U-shaped channel is closed by an end wall which includes a tubular nipple extending beyond said upper blade member proximate its pivotal connection with said slide member, said tubular nipple adapted to connect to a suction hose to induce the flow of smoke through said smoke evacuation passage.

4. The speculum according to claim 2 wherein said U-shaped channel member has a cross-sectional area with dimensions selected to provide a sufficient rate of smoke removal such that the smoke will not obscure light transmitted along said light pipe.

5. The speculum according to claim 1 further including adjustable extension means including a pawl projecting from said slide member and a series of ratchet teeth formed on the leg portion engagable by the slide member pawl which is biased toward the leg portion teeth, said adjustable extension means for locking said slide member in an adjusted position relative to said leg portion, when positioning the upper blade in an extended position relative to the lower blade.

6. The speculum according to claim 1 further including adjustable rotation means including a lever portion projecting from said upper blade adjacent its pivotal connection with said slide member and a curved ratchet-toothed tongue projecting from said slide member toward said lever portion, said lever portion having a pawl engagable by the ratchet teeth of the tongue which is biased toward the lever portion pawl by the resiliency of the plastic material forming said slide member, said adjustable rotation means for locking the blade members in an adjusted angular position relative to each other, said slide member, its pawl, and its curved ratchet-toothed tongue being formed as a single-piece unit from said relatively flexible plastic material.

7. A smoke evacuation assembly for use in the upper blade member of a vaginal speculum to remove smoke produced by various surgical procedures, said smoke evacuation assembly comprising:

a U-shaped channel member adapted to be positioned adjacent a contoured interior surface of the upper blade member, said U-shaped channel member including a forward end, a rearward end, a bottom surface, and a pair of opposed side walls each having a top edge shaped to fit snugly against the contours of the interior surface to thereby form a smoke evacuation passage;

a tubular nipple formed in an end wall closing said rearward end of the U-shaped channel and extending beyond the upper blade member, said tubular nipple adapted to connect to a suction hose to induce the flow of smoke through said smoke evacuation passage so that smoke being removed through the passage travels from said forward end toward said rearward end while being substantially retained within said U-shaped channel member and a pair of retaining walls formed along contoured interior surface of said upper blade member, said retaining walls providing an interlocking sliding fit with said pair of opposed side walls of said U-shaped channel member.

* * * * *